(12) United States Patent
Oonaka et al.

(10) Patent No.: US 7,393,641 B2
(45) Date of Patent: Jul. 1, 2008

(54) METHOD OF DETECTING MICROMETASTASIS

(75) Inventors: Satoru Oonaka, Tokyo (JP); Toshinori Hayashi, Kanagawa-ken (JP)

(73) Assignee: Tosoh Corporation, Shunan-shi (JP)

( * ) Notice: Subject to any disclaimer, the term of this patent is extended or adjusted under 35 U.S.C. 154(b) by 486 days.

(21) Appl. No.: 10/839,202

(22) Filed: May 6, 2004

(65) Prior Publication Data

US 2004/0224342 A1    Nov. 11, 2004

(30) Foreign Application Priority Data

May 7, 2003    (JP)    ............................ 2003-129360

(51) Int. Cl.
  *C12Q 1/68*   (2006.01)
  *C07H 21/04*  (2006.01)
  *C12P 19/34*  (2006.01)

(52) U.S. Cl. ........................ 435/6; 536/24.3; 435/91.2

(58) Field of Classification Search ........................ None
  See application file for complete search history.

(56) References Cited

U.S. PATENT DOCUMENTS

| | | | | |
|---|---|---|---|---|
| 6,057,105 | A  * | 5/2000  | Hoon et al. | 435/6 |
| 6,329,179 | B1 * | 12/2001 | Kopreski | 435/91.2 |
| 7,056,660 | B1 * | 6/2006  | Giesing et al. | 435/6 |
| 2002/0098492 | A1 * | 7/2002 | Taya | 435/6 |

FOREIGN PATENT DOCUMENTS

| | | |
|---|---|---|
| WO | WO 96/29430  | 9/1996 |
| WO | WO 97/18322  | 5/1997 |
| WO | WO 99/32644  | 7/1999 |
| WO | WO 01/18245  | 3/2001 |
| WO | WO 01/49716  | * 7/2001 |
| WO | WO 02/12328  | 2/2002 |
| WO | WO 03/085087 | * 10/2003 |

OTHER PUBLICATIONS

GENBANK Accession M29540 GI: 180222 PRI Nov. 1994.*
Deiman, Birgit et al. Characteristics and Applications of Nucleic Acid Sequence Based Amplification. 2002 Moleuclar Biotechnology. vol. 20 pp. 163-179.*
A. C. Lambrechts, et al., Breast Cancer Research and Treatment, vol. 56, No. 3, XP-009035704, pp. 219-231, "Comparison of Immunocytochemistry, Reserve Transcriptase Polymerase Chain Reaction, and Nucleic Acid Sequence-Based Amplification for the Detection of Circulating Breast Cancer Cells", Aug. 1999.
H. Nogi, et al., Breast Cancer, vol. 10, No. 1, XP-009035695, pp. 74-81, "Detection of MUC1 and Keratin 19 mRNAs in the Bone Marrow by Quantitative RT-PCR Predicts the Risk of Distant Metastasis in Breast Cancer Patients", Jan. 2003.
Schrewe, H. et al., "Cloning of the complete gene for carcinoembryonic antigen: analysis of its promoter indicates a region conveying cell type-specific expression", Mol. Cell. Biol. 10 (6), 1990, pp. 2738-2748, M59256, Reports, Nucleotide, 2 pages.
Article on the "Preparation and Utilization of Isolated and Purified Oligonucleotides" by Andrew Chin, Mar. 9, 2002 (Paper Copy & CD.

* cited by examiner

*Primary Examiner*—Juliet C. Switzer
*Assistant Examiner*—Amanda Shaw
(74) *Attorney, Agent, or Firm*—Oblon, Spivak, McClelland, Maier & Neustadt, P.C.

(57) ABSTRACT

A method of detecting micrometastasis of tumor cells in a sample obtained from a region of a subject other than the primary focus of the tumor by using a first primer complementary to part of a specific sequence in the RNA from tumor cells and a second primer homologous to part of the specific sequence (either of which additionally has a promoter sequence for an RNA polymerase at the 5' end), which comprises (1) synthesizing a cDNA by the action of an enzyme having RNA-dependent DNA polymerase activity by using the specific sequence as a template, (2) degrading the RNA strand in the RNA-DNA double strand by an enzyme having a ribonuclease H activity (to give a single-stranded DNA), (3) forming a double-stranded DNA having a promoter sequence which can be transcribed into an RNA homologous or complementary to the specific sequence by using the single-stranded DNA as a template by the action of an enzyme having DNA-dependent DNA polymerase activity, and (4) transcribing the double-stranded DNA into an RNA transcript (which acts as a template in the subsequent cDNA synthesis in the reaction (1)) by the action of an enzyme having RNA polymerase activity and detecting the mRNA.

7 Claims, 4 Drawing Sheets

Figure 1:
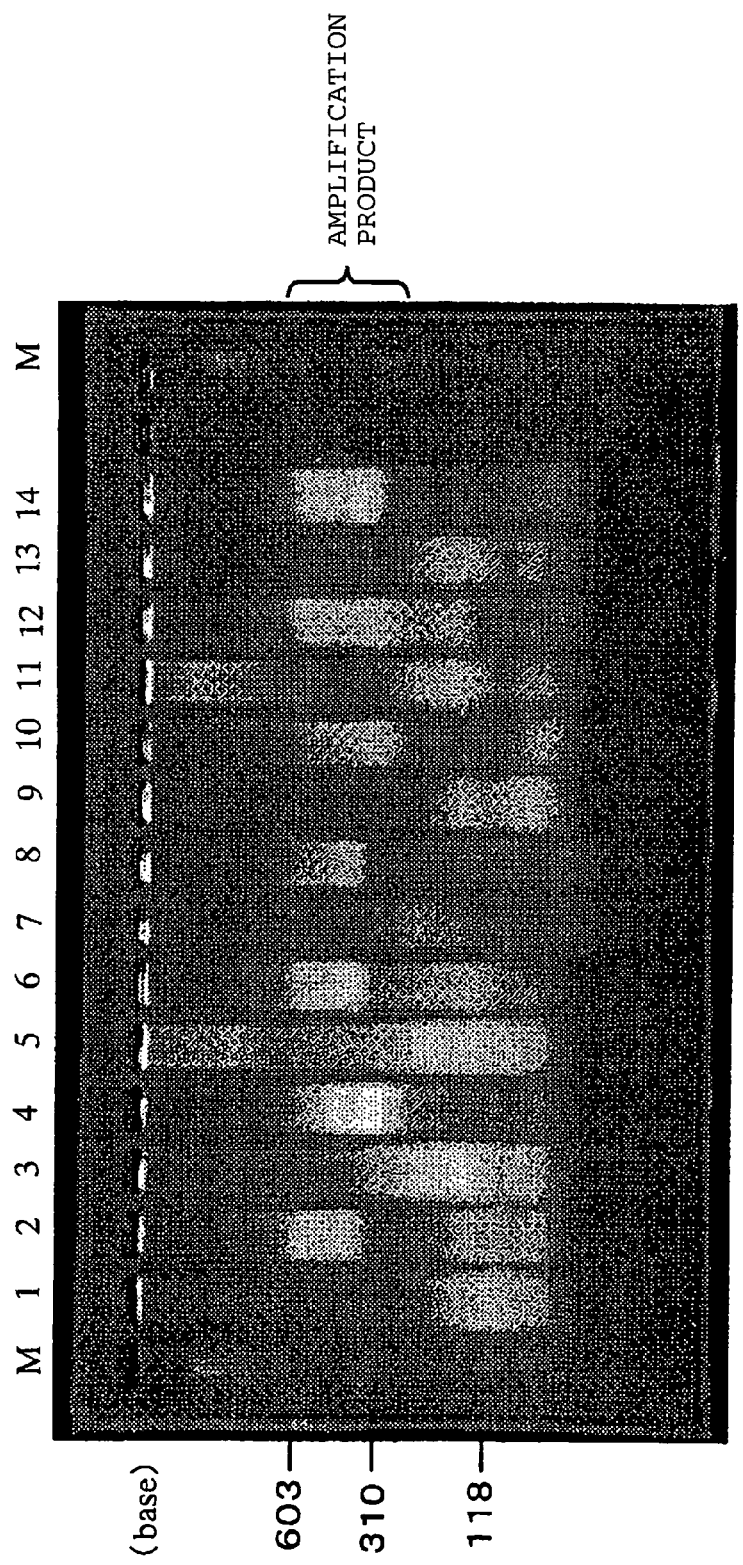

B¹, B², B³ and B⁴ are bases

METHOD OF DETECTING MICROMETASTASIS

The present invention relates to a method of detecting micrometastasis of tumor cells, polynucleotides suitable for use in the method as the primers or the like (for detection of CEA) and a kit for detection of micrometastasis of tumor cells comprising the polynucleotides. The method of the present invention of detecting micrometastasis of tumor cells is a fast method which enables one step isothermal amplification and detection of a tumor cell RNA and can be carried out, for example, before surgical removal of tumor cells.

Carcinoma cells disseminate from primary tumors hematogenously or lymphatically to develop distant micometastasis. Because successful resection of primary foci can not always prevent tumor recurrence due to micrometastasis, it is surgically common to resect all lymph nodes not only from primary tumors but also from their peripheries (radical lymph node dissection). Though radical lymph node dissection may prevent recurrences, there is a problem that many patients suffer sequelae such as swelling which inevitably lower their quality of life.

Therefore, current tumor surgery is aimed for preventing recurrences with minimal section areas. For this purpose, exact identification of micrometastases is essential. However, preoperative micrometastasis detection by diagnostic imaging is not sensitive or specific enough, and therefore, intraoperative microscopic examination of representative samples from patient tissues is necessary.

Recently, detection of tumor cells by RT-PCR amplification-based assay of the mRNA expressed by cancer specific genes has been studied extensively (non-patent documents 1 to 3).

The RT-PCR assays disclosed in non-patent documents 1 to 3 entail repetitive rapid heating and cooling of reaction solutions which is cumbersome enough to require a lot of skill and have the problem that they require at least two steps for reverse transcription and PCR amplification. Therefore, RT-PCR assays not only take long time to give results (for example, usually, from 30 to 60 minutes for reverse transcription and from 30 to 60 minutes for PCR) but also require care so as to avoid contamination among samples between RT and PCR. A one step RT-PCR assay has been developed so far, and it is time-saving tough, its detection limit is still insufficient at a level of from $10^3$ to $10^5$ copies.

Further, improvement of the sensitivity of RT-PCR assays necessitates optimization of amplification conditions such as heating and cooling conditions for each target RNA to be amplified and detected. However, for detection of micrometastasis, it is sometimes necessary to amplify and detect the mRNAs of plural tumor markers such as CEA (carcinoembryonic antigen), cytokeratin 20, β-actin, mammagloblin A, SCC antigen (squamous cell carcinoma antigen) and PBGD (porphobilinogen deaminase) simultaneously. In such cases, mRNAs having different optimal amplification and detection conditions are practically difficult to handle with a single thermocycler and have to be detected separately, and, as a result, delays assay results.

Some RNA amplification methods which give RNA as the amplification product with no need for heating or cooling of reaction solutions, unlike RT-PCT in which cDNA reverse-transcript from RNA is amplified by heating and cooling the reaction solution, have been reported (for example, NASBA disclosed in patent document 1, TMA disclosed in patent document 2 and the amplification and detection method disclosed in patent document 3). These methods involve synthesis of double-stranded DNA having a promoter sequence for an RNA polymerase, which is transcribed into an RNA transcript having a specific sequence.

More specifically, in the case of an arbitrary RNA, (1) an RNA-dependent DNA polymerase (reverse transcriptase) synthesizes the DNA complementary to a specific sequence in the RNA which distinguishes it from other RNAs by using a DNA primer complementary to a 3' region of the specific sequence and the RNA as the template, (2) an enzyme having ribonuclease H activity degrades the RNA strand in the RNA-DNA double strand produced by the reverse transcription to leave a single-stranded DNA behind, (3) a DNA-dependent DNA polymerase synthesizes a double-stranded DNA having a promoter sequence for an RNA polymerase by using a DNA primer which is complementary to a 3' region of the single strand and has the above-mentioned promoter sequence at the 5' end, and (4) an RNA polymerase transcribes the double-stranded DNA to give a transcript (an RNA having the specific sequence). The RNA transcript having the specific sequence serves as the template for the above-mentioned reaction (1) and hybridizes with the DNA primer used in the above-mentioned reaction (1) to provoke the reaction (2) and the subsequent reactions, and the chain reaction proceeds to amplify the RNA.

These methods are characterized in that it is not necessary to heat and cool the reaction solution as in PCR or carry out RNA reverse transcription and the subsequent amplification separately.

The object of the present invention is to provide a method of detecting micrometastasis of tumor cells isothermally in one step quickly (for example, intraoperatively) in which these methods are applied to amplification and detection of an RNA from tumor cells in a sample obtained from a region of a subject other than the primary focus of the tumor.

[Non-patent document] Palmieri G., Ascierto P A. Et al., Journal of Clinical Oncology, 19, 1437-1443 (2001)

[Non-patent document 2] Nogi H. Takeyama H., et al, Breast Cancer, 10, 74-81 (2003)

[Non-patent document 3] Hampton R., Walker M., et al., Oncogene, 21. 7817-7823 (2002)

[Patent document 1] JP Patent No. 2650159

[patent document 2] JP Patent No. 3241717

[patent document 3] JP-A-2000-14400

The present invention has been accomplished to attain the above-mentioned object. The invention defined in claim 1 of the present application provides a method of detecting micrometastasis of tumor cells in a sample obtained from a region of a subject other than the primary focus of the tumor by using a first primer complementary to part of a specific sequence in the RNA from tumor cells and a second primer homologous to part of the specific sequence (either of which additionally has a promoter sequence for an RNA polymerase at the 5' end), which comprises (1) synthesizing a cDNA by the action of an enzyme having RNA-dependent DNA polymerase activity by using the specific sequence as a template, (2) degrading the RNA strand in the RNA-DNA double strand by an enzyme having a ribonuclease H activity (to give a single-stranded DNA), (3) forming a double-stranded DNA having a promoter sequence which can be transcribed into an RNA homologous or complementary to the specific sequence by using the single-stranded DNA as a template by the action of an enzyme having DNA-dependent DNA polymerase activity, and (4) transcribing the double-stranded DNA into an RNA transcript (which acts as a template in the subsequent cDNA synthesis in the reaction (1)) by the action of an enzyme having RNA polymerase activity and detecting the mRNA.

The invention defined in claim 2 of the present application provides the method according to claim 1, wherein the RNA from tumor cells is carcinoembryonic antigen (CEA) RNA.

The invention defined in claim 3 of the present application provides a polynucleotide favorably used in the method according to claim 1 as primers and the like, which comprises a sequence homologous or complementary to at least 10 consecutive nucleotides in any of SEQ ID NOS:1 to 22.

The invention defined in claim 4 of the present application provides a kit for detection of micrometastasis of tumor cells, which comprises the polynucleotide according to claim 3.

FIG. 1 shows the results of RNA amplification using various combinations of primers at an initial RNA amount of $10^4$ copirs/30 µl. Nega denotes a sample consisting of a diluent only instead of an RNA sample. Lane 1: combination 1 with nega. Lane 2: combination 1 at $10^4$ copies. Lane 3: combination 2 with nega. Lane 4: combination 2 at $10^4$ copies. Lane 5: combination 3 with nega. Lane 6: combination 3 at $10^4$ copies. Lane 7: combination 4 with nega. Lane 8: combination 4 at $10^4$ copies. Lane 9: combination 5 with nega. Lane 10: combination 5 at $10^4$ copies. Lane 11: combination 6 with nega. Lane 12: combination 6 at $10^4$ copies. Lane 13: combination 7 with nega. Lane 12: combination 7 at $10^4$ copies. Within the brace are specifically amplified bands which the respective oligonucleotide combinations gave.

Figure 2:
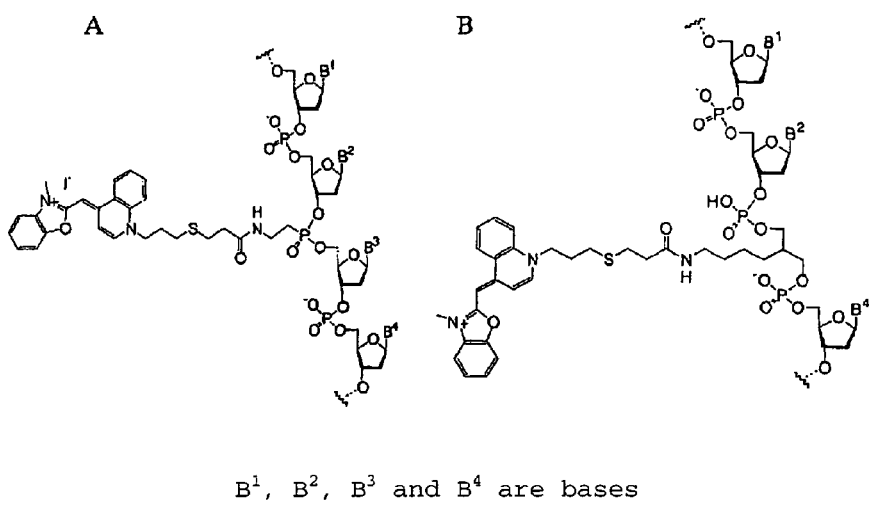

FIG. 2 shows chemical structures of the binding of the fluorescent intercalative dye (oxazole yellow) in the fluorescent intercalative dye-labeled oligonucleotide used in Examples 2 to 4, wherein $B^1$, $B^2$, $B^3$ and $B^4$ are nucleic acid bases, prepared in accordance with Ishiguro, T (1996) Nucleic Acids Res., 24 (24) 4992-4997 (FIG. 2A) and by introducing a functional group in the nucleotide chain with Label-ON Reagents (Clontech) (FIG. 2B).

Figure 3:
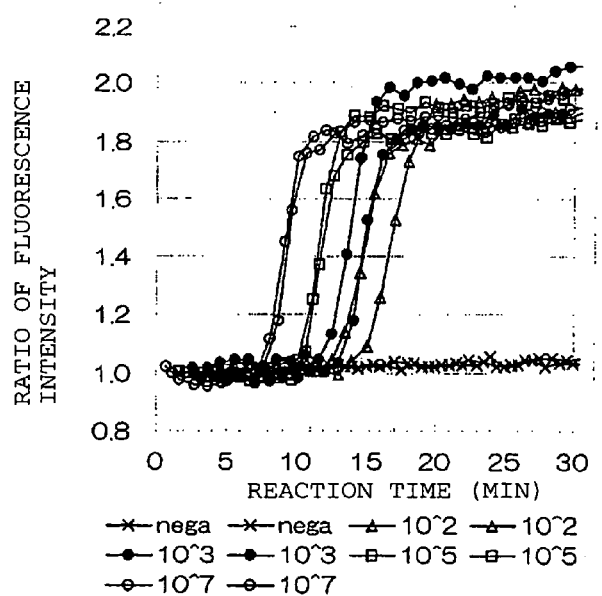

FIG. 3 is a graph showing the fluorescence enhancement which increases with reaction time and RNA synthesis at initial RNA amounts of from $10^7$ copies/30 µl to $10^2$ copies/30 µl. For nega, only the diluent was used instead of the RNA sample.

Figure 4:
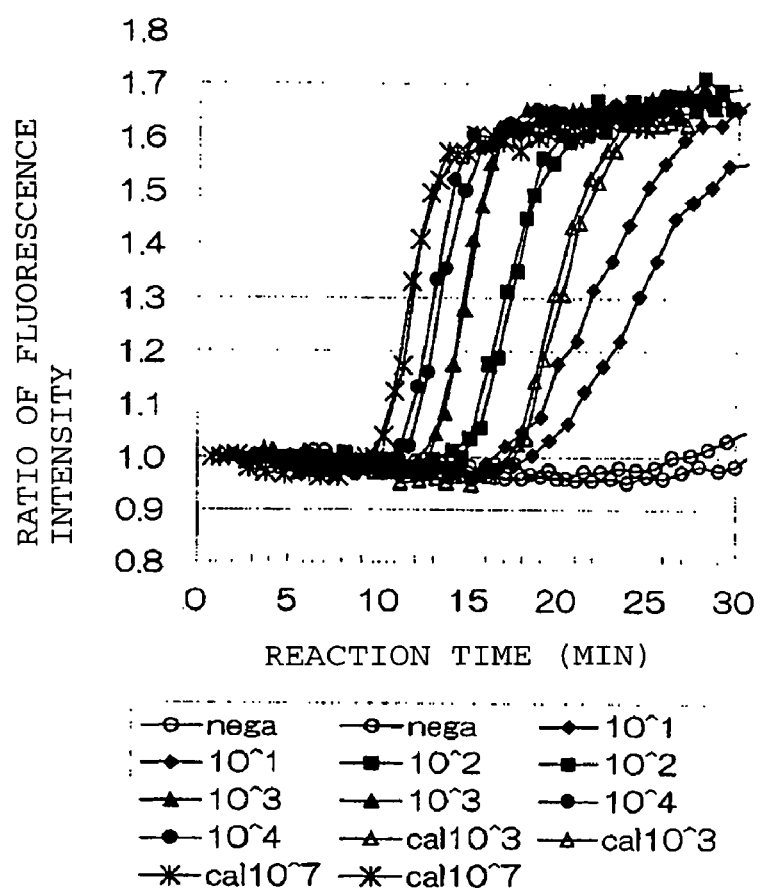

FIG. 4 is a graph showing the results of the MKN45 RNA assay with the same reaction solutions as in Example 3. Nega: a sample consisting of a diluent only instead of an RNA sample. $10^4$: MKN45 RNA equivalent to $10^4$ MKN45 cells. $10^3$: MKN45 RNA equivalent to $10^3$ MKN45 cells mixed with white blood cell RNA equivalent to $10^4$ normal white blood cells. $10^2$: MKN45 RNA equivalent to $10^2$ MKN45 cells mixed with white blood cell RNA equivalent to $10^4$ normal white blood cells. $10^1$: MKN45 RNA equivalent to $10^1$ MKN45 cells mixed with white blood cell RNA equivalent to $10^4$ normal white blood cells. Nega: white blood cell RNA equivalent to $10^4$ normal white blood cells. cal10^7: CEA RNA $10^7$ copies/5 µL. cal10^3: CEA RNA $10^3$ copies/5 µL.

Figure 5:
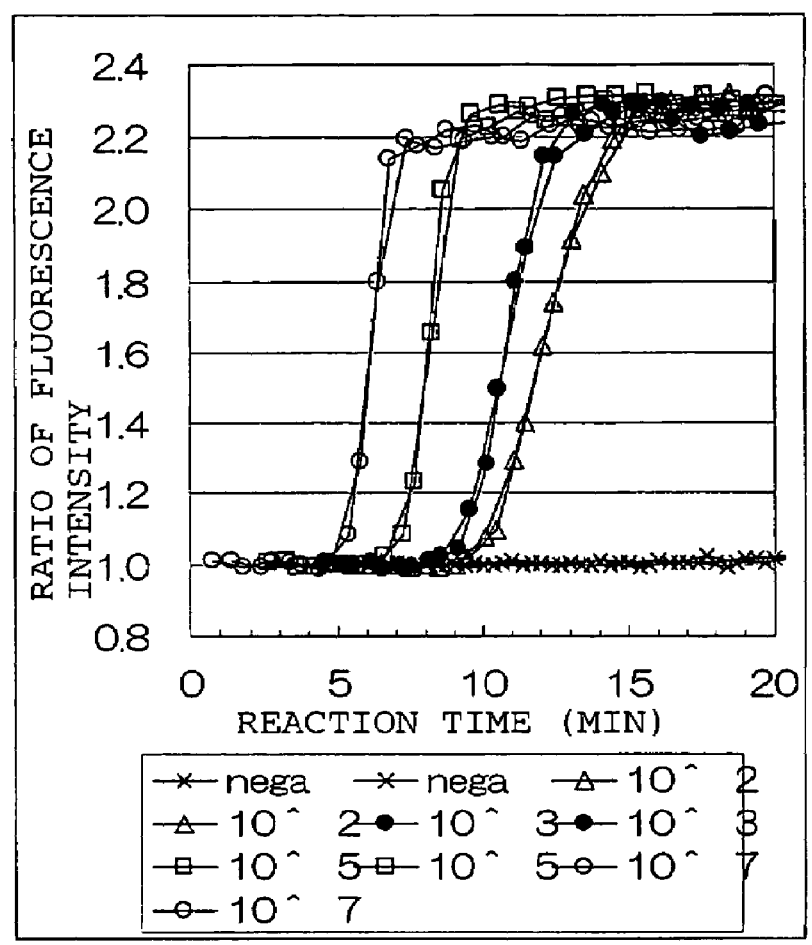

FIG. 5 is a graph showing the fluorescence enhancement which increases with reaction time and RNA synthesis at initial RNA amounts of from 107 copies/30 µl to 102 copies/30 µl. For nega, only the diluent was used instead of the RNA sample.

Now, the present invention will be described in detail.

The present invention uses RNA amplification which gives RNA as the amplification product to make it possible to detect micrometastasis of tumor cells isothermally in one step quickly (for example, intraoperatively). Especially, addition of a fluorescent intercalative dye-labeled oligonucleotide probe hybridizable with the transcript (JP Patent No. 3189000) to the reaction solution makes it possible to amplify the specific or complementary sequence and detect (monitor) the way it is amplified. The probe used for monitoring is obtained by liking a fluorescent intercalative dye to an oligonucleotide hybridizable with the specific or complementary sequence so that the fluorescent intercalative dye alters its fluorescence upon hybridization with the transcript. The above-mentioned monitoring is the most suitable mode of carrying the present invention. Though there is no particular restriction on how to link the fluorescent intercalative dye as the label to the oligonucleotide, it is preferred to link the fluorescent intercalative dye to a phosphorus atom via a linker. They may be liked, for example, by introducing a functional group such as an amino group into the oligonucleotide chain or at either end of the oligonucleotide, then optionally introducing a functional group reactive or linkable with the functional group introduced to the oligonucleotide into the fluorescent intercalative dye, and bonding the two functional groups. The details are disclosed in JP-A-2000-154431 or Ishiguro, T (1996) Nucleic Acids Res. 24 (24) 4992-4997 (FIG. 2A in the present application). A functional group may be introduced into the oligonucleotide chain or at the end of the oligonucleotide by any methods, for example, by using Label-ON Reagents (Clontech) (FIG. 2B).

The present invention is carried out isothermally at relatively low temperatures of from 35° C. to 50° C. (preferably 44° C.). The present invention is used for s samples obtained from a region of a subject other than the primary focus of the tumor to detect micrometastasis of tumor cells. The tumor cells examined for metastasis by the present invention are not particularly restricted and may be tumor cells transcribing a unique RNA or expressing an arbitrary RNA, though not unique, in an abnormal amount.

In the present invention, the RNA as the direct amplification and detection target for detection of tumor cell micrometastasis may, for example, the mRNA transcribed from an oncogene such as src, erbB, sis, ras, myc or fos, the mRNA transcribed from BCR-ABL, PML-RARA, DEK-CAN or E2A-PBX, the mRNA transcribed from a gene encoding an oncofetal protein such as CEA (carcinoembryonic antigen), AFP (alpha fetoprotein), POA (pancreatic oncofetal antigen), NSE (neuron specific enolase), SCC (squamous cell carcinoma antigen), PSA (prostate specific antigen), BFP (basic fetoprotein), γSm (γ-seminoprotein), SP1 (β1-glycoprotein), CAF (carcinoembryonic fibronectin), cytokeratin 19, cytokeratin 20, mammaglobin or α macroglobin, the mRNA transcribed from a gene encoding elastase-1 as an oncogenic ectopic product or an oncogenic isozyme such as ALP (alkaline phosphatase), PAP (prostate acid phosphatase) or ICDH (isocitric acid dehydrogenase), the mRNA transcribed from a gene encoding a hormone such as ADH (antidiuretic hormone), ACTH (adorenocorticotropic hormone), CRF (cortikotrophin-releasing factor), FSH (follicle-stimulating hormone), PRL (prolactin), PTH (parathyroid hormone), βHCG (β human chorionic gonadotropin), PTHrP (parathyroid hormone-related peptide) or calcitonin or the mRNA transcribed from a gene encoding an carcionomatous abnormal protein (polypeptide) such as IAP (immunosuppressive acid protein), PIVKA II (protein induced by vitamin K absence or antagonist), TPA (tissue polypeptide antigen) or SHBG (sex hormone binding globulin). In particular, CEA RNA is an RNA peculiar to tumor cells which is hardly transcribed in normal cells and, therefore, is a preferable amplification and detection target.

To carry out the present invention, the target RNA is first selected, then a specific sequence in the RNA is selected, and the sequences of the first and second primers used in the present invention are designed for the selected specific sequence. For example, oligonucleotides containing a sequence homologous or complementary to at least 10 consecutive nucleotides in SEQ ID NOS:1 to 22 are preferable examples of the primer used for detection of the mRNA transcribed from the CEA gene as described in Examples.

The primary focus of the tumor is the place where the tumor has originated. In the present invention, samples from other regions than the primary focus of the tumor are used. The samples means RNA-containing nucleic acid samples. In the present invention, samples prepared from tissues from other regions of a subject than the primary focus of the tumor according to the procedure disclosed in JP-A-7-59572, for example, are used, and an RNA as exemplified above is directly amplified and detected to determine whether tumor cells have micrometastasized to the tissues from which the samples are obtained.

The present invention will be described in further detail below. When a tumor cell RNA as the amplification and detection target is present in a sample, (1) the first primer (complementary to a 3' region of the specific sequence) hybridizes with the specific sequence in the RNA and elongates as a cDNA along the specific sequence in the RNA as the template by the action of an RNA-dependent DNA polymerase to form a RNA-DNA double strand, (2) then, the RNA in the RNA-DNA double strand is degraded by an enzyme having ribonuclease H activity to leave a single-stranded DNA, (3) the second primer (which is homologous to a 5' region of the target RNA and additionally has a promoter sequence for an RNA polymerase at the 5' end) hybridizes with the single-stranded DNA to direct an enzyme having DNA-dependent DNA polymerase activity to form a double-stranded DNA having a promoter sequence which is transcribed into an RNA homologous to the target RNA sequence, and (4) the double-stranded DNA is transcribed by an enzyme having RNA polymerase activity into an RNA transcript homologous to the specific sequence. Since the RNA transcript having the specific sequence serves as the template for the reaction (1), the above-mentioned reactions (1) to (4) proceed sequentially until the enzymes which catalyze RNA and DNA syntheses run out of their substrates or inactivate.

In the above-mentioned embodiment, a second primer additionally having a promoter sequence for the RNA polymerase at the 5' end is used (hereinafter referred to as the first embodiment). In the present invention, a first primer additionally having a promoter sequence for the RNA polymerase at the 5' end may be used (hereinafter referred to as the second embodiment). In the first embodiment of the present invention, in order to improve the sensitivity by amplifying the specific sequence more efficiently, the RNA containing the specific sequence has to be cleaved at the 5' end of the specific sequence prior to the above-mentioned reaction (1) (patent document 3).

For the RNA cleavage, the enzyme having ribonuclease H activity, which is used in the subsequent reactions, for example, may be used in the presence of an oligonucleotide (scissor oligonucleotide) complementary to a region of the RNA which flanks the 5' end of the specific sequence with an overlap. Preliminary treatment such as amination of the 3' end of the scissor oligonucleotide is preferred to prevent the oligonucleotide from serving as a primer.

For detection of tumor cell micrometastasis, it is necessary to check for the presence of the specific sequence by detecting the presence of the amplified specific sequence or to estimate the amount of the specific sequence present in a sample (number of copies of the target RNA) from the amount (number of RNA copies) of the amplified specific sequence. The specific sequence may be detected by sandwich assay with reaction solutions using immobilized and labeled probes hybridizable with the specific sequence after the above-mentioned reactions are performed for a predetermined time. However, it is preferred to use a fluorescent intercalative dye-labeled oligonucleotide probe which is hybridizable with the specific sequence. Since the probe does not interfere with the reaction (4), it is particularly preferred to amplify the specific sequence in its presence and monitor the amplification of the specific sequence. When the specific sequence is amplified in the presence of a fluorescent intercalative dye-labeled oligonucleotide probe, preliminary addition of glycolic acid, biotin or the like to the 3' end is preferable to prevent the probe from elongating like a primer. During the amplification, the fluorescent signal from the fluorescent intercalative dye-labeled oligonucleotide probe hybridized with the specific sequence is measured with a fluorometer. Comparison of the information given by the fluorescent profile (such as the amplification time required until the fluorescence intensity of the fluorescent dye reaches a certain level) with the information obtained from a fluorescent profile for a known amount of the standard RNA makes it possible to determine the presence or absence of the specific sequence or estimate the amount of the specific sequence present in the sample (number of copies of the target RNA) from the amount (number of RNA copies) of the amplified specific sequence.

Assembling a ready-made detection kit greatly facilitates the method of the present invention as described above. The detection kit preferably contains all the reagents necessary for amplification and detection of the specific sequence such as the first and the second primer, the scissor primer (in the case of the first embodiment), the fluorescent intercalative dye-labeled oligonucleotide probe, an enzyme having RNA-dependent DNA polymerase activity, an enzyme having ribonuclease H activity, an enzyme having DNA-dependent DNA polymerase activity, an enzyme having RNA polymerase activity and the substrates for these enzymes. It is noteworthy that all the reagents can be put in a single vessel. Namely, just dispensing a certain amount of a sample into the single vessel provokes amplification and detection of the tumor cell RNA automatically. The only requirement for the vessel is that it is partly transparent so that the signal from the fluorescent dye can be measured from the outside. Vessels which can be sealed after samples are dispensed are particularly preferable to prevent contamination.

Now, the present invention will be described in further detail by referring to Examples. However, the present invention is by no means restricted to these specific Examples.

EXAMPLE 1

Carcinoembryonic antigen (CEA) RNA was amplified specifically using combinations of oligonucleotide primers of the present invention. The CEA RNA was prepared by in vitro transcription of a double-stranded DNA containing the nucleotide sequence of CEA gene (National Center Biotechnology Information accession No.: M29540) and isolated. In this present Example, the specific sequences mean those of the transcription products shown later in Table 1.

(1) The CEA RNA (2109-mer) as the sample was quantified by UV absorptiometry at 260 nm and diluted to $1.0 \times 10^4$ copies/5 µl with an RNA diluent (10 mM Tris-HCl (pH 8.0), 0.1 mM EDTA, 0.5 U/µl RNase inhibitor, 5.0 mM DTT). As the control (nega), the diluent was used.

(2) 20.8 µl portions of a reaction solution of the following composition were dispensed into 0.5 ml PCR tubes (Gene Amp Thin-Walled Reaction Tubes, Perkin Elmer), and 5.0 µl of the above-mentioned CEA RNA sample was added.

The composition of the reaction solution (in terms of the final concentration in the reaction solutions after the addition of an enzyme solution)
  60.0 mM Tris-HCl buffer (pH 8.6)
  17.0 mM Magnesium chloride
  100.0 mM Potassium chloride
  1.0 mM DTT
  6 U RNase Inhibitor (Takara Bio)
  0.25 mM dATP, dCTP, dGTP, dTTP
  3.0 mM ATP, CTP, UTP
  2.25 mM GTP
  3.6 mM ITP
  1.0 µM each of a first oligonucleotide primer and a second oligonucleotide primer (having the sequences shown in Table 1 and used in the combinations shown in Table 1 (The second oligonucleotide primers additionally had SEQ ID NO:23 (the promoter sequence for T7 polymerase) at the 5' end))
  0.16 µM a scissor oligonucleotide (for cleavage of the target RNA at the site of hybridization with the second primer and having an aminated 3' end (Table 1))
  13.0% DMSO
  Distilled water for volume adjustment

TABLE 1

| Combination | First primer | Second primer | Scissor primer | Length of amplification product (mer) |
|---|---|---|---|---|
| 1 | SEQ ID NO:1 | SEQ ID NO:7 | SEQ ID NO:13 | 332 |
| 2 | SEQ ID NO:2 | SEQ ID NO:8 | SEQ ID NO:14 | 238 |
| 3 | SEQ ID NO:3 | SEQ ID NO:8 | SEQ ID NO:14 | 313 |
| 4 | SEQ ID NO:4 | SEQ ID NO:9 | SEQ ID NO:15 | 318 |
| 5 | SEQ ID NO:4 | SEQ ID NO:10 | SEQ ID NO:16 | 243 |
| 6 | SEQ ID NO:5 | SEQ ID NO:11 | SEQ ID NO:17 | 253 |
| 7 | SEQ ID NO:6 | SEQ ID NO:12 | SEQ ID NO:18 | 357 |

(3) The reaction solutions were incubated at 44° C. for 5 minutes, and 5.0 µl of an enzyme solution of the following composition preincubated at 44° C. for 2 minutes was added.

The composition of the enzyme solution (in terms of the final concentration at the time of the reaction)
  2.0% Sorbitol
  8 U AMV reverse transcriptase (Takara Bio)
  142 U T7 RNA polymerase (GIBCO)
  3.6 µg Bovine serum albumin
  Distilled water for volume adjustment (4) Then, the PCR tubes were incubated at 44° C. for 30 minutes, and the specific amplification products were analyzed by 3% agarose gel electrophoresis.

(5) The electrophoresis was followed by staining with SYBR Green II (Takara Shuzo).

The results of the electrophoresis are shown in FIG. 1. All the combinations gave specific RNA amplification products, i.e., the amplified specific sequences (within the brace in FIG. 1) and proved to be useful for amplification of the RNA from CEA.

EXAMPLE 2

A fluorescent intercalative dye-labeled oligonucleotide probe was prepared.

A 20-mer oligonucleotide having the sequence shown in SEQ ID NO:19 was modified by attaching an amino group between the 5th nucleotide (G) and the 6th nucleotide (A) from the 5' end via a $C_{15}$ linker with Label-ON Reagents (Clontech), and its 3' end was further modified with biotin.

Oxazole yellow, a conventional fluorescent intercalative dye, was attached as the label to give an oxazole yellow-labeled oligonucleotide probe (SEQ ID NO:19) (FIG. 2B, Ishiguro, T (1996) Nucleic Acids Res. 24 (24) 4992-4997).

EXAMPLE 3

CEA RNA at various initial copy numbers was detected using the combinations of oligonucleotide primers of the present invention.

The CEA RNA (2109-mer) as the sample was quantified by UV absorptiometry at 260 nm and diluted to $1.0 \times 10^7$ to $10^2$ copies/5 µl with an RNA diluent (10 mM Tris-HCl (pH 8.0), 0.1 mM EDTA, 0.5 U/µl RNase inhibitor, 5.0 mM DTT). As the control (nega), the diluent was used.

20.0 µl portions of a reaction solution of the following composition were dispensed into 0.5 ml PCR tubes (Gene Amp Thin-Walled Reaction Tubes, Perkin Elmer), and 5.0 µl of the above-mentioned CEA RNA sample was added.

The composition of the reaction solution (in terms of the final concentration in the reaction solutions after the addition of an enzyme solution)
  60.0 mM Tris-HCl buffer (pH 8.6)
  17.0 mM Magnesium chloride
  100.0 mM Potassium chloride
  1.0 mM DTT
  0.25 mM dATP, dCTP, dGTP, dTTP
  3.0 mM ATP, CTP, UTP
  2.25 mM GTP
  3.6 mM ITP
  1.0 µM First oligonucleotide primer (SEQ ID NO:20) and second oligonucleotide primer (SEQ ID NO:12) (The second oligonucleotide primer additionally had SEQ ID NO:23 (the promoter sequence for T7 polymerase) at the 5' end))
  0.16 µM Scissor oligonucleotide (SEQ ID NO:18; for cleavage of the CEA RNA at the site of hybridization with the second primer and having an aminated 3' end)
  6 U RNase Inhibitor (Takara Bio)
  13.0% DMSO
  Distilled water for volume adjustment
  15.0 nM Fluorescent intercalative dye-labeled oligonucleotide probe (prepared in Example 2)

(3) The reaction solutions were incubated at 44° C. for 5 minutes, and 5.0 µl of an enzyme solution of the following composition preincubated at 44° C. for 2 minutes was added.

The composition of the enzyme solution (in terms of the final concentration at the time of the reaction)
  2.0% Sorbitol
  8 U AMV reverse transcriptase (Takara Bio)
  142 U T7 RNA polymerase (GIBCO)
  3.6 µg Bovine serum albumin
  Distilled water for volume adjustment (4) The fluorescence intensities of the reaction solutions in the PCR tubes were directly monitored at 44° C. in a thermostatic fluorescent spectrophotometer at an excitation wavelength of 470 nm and an emission wavelength of 510 nm.

FIG. 3 shows the time courses of the ratio of fluorescence intensities of the samples (fluorescence intensity at a certain time/background fluorescence intensity) from addition of the enzyme solution at 0 minute at the initial amounts of the CEA RNA of from $10^7$ copies/30 µl to $10^2$ copies/30 µl. The fluorescence profiles were dependent on the initial CEA RNA concentrations as shown in FIG. 3 and suggest that it is possible to quantify the CEA RNA in an unknown sample.

EXAMPLE 4

The expression of CEA RNA by a poorly differentiated gastric cancer cell line MKN45 was actually measured with an oligonucleotide primer combination of the present invention.

(1) Sampling

Poorly differentiated MKN45 gastric cancer cells were cultured in RPMI 1640 medium (supplemented with 10% FCS), harvested from the dish by trypsin treatment, separated from the medium by centrifugation and washed with phosphate buffered saline. The cell pellets were lysed in 0.5 mL TRIZOL reagent (Invitrogen).

Normal white blood cells were separated from blood donated by healthy employee volunteers using Mono-Poly Resolving Medium (Dainippon Pharmaceutical) and lysed in 0.5 mL TRIZOL reagent.

(2) RNA Isolation

The lysates of $10^6$ MKN45 cells and $10^6$ normal white blood cells (in 0.5 mL TRIZOL reagent) were put in 1.5 mL Eppendorf tubes and homogenized with a disposable homogenizer (Ieda Chemicals). The homogenates were incubated for 5 minutes at room temperature, vortexed with 0.2 mL of chloroform for 15 minutes, allowed to stand for 4 minutes at room temperature and centrifuged at 4° C. for 15 minutes at 12000×G. The supernatants were transferred to fresh Eppendorf tubes, mixed with 0.5 mL propanol by shaking, allowed to stand for 10 minutes at room temperature and centrifuged at 4° C. for 15 minutes at 12,000×G. After removal of the supernatants, the pellets were mixed with 1 mL 75% aqueous ethanol and centrifuged at 4° C. for 5 minutes at 7500×G. The supernatants were removed, and the pellets were air-dried for 1 hour and then dissolved in an RNA diluent (10 mM Tris-HCl (pH 8.0), 0.1 mM EDTA, 0.5 U/µl RNase inhibitor, 5.0 mM DTT). The RNA concentration measurement by absorptiometry at 260 nm revealed that 10.7 µg of RNA was isolated from $10^6$ MKN45 cells, while 12.2 µg of RNA was isolated from $10^6$ normal white blood cells.

(3) MKN45 RNA Assay

The reaction solutions having the same compositions as in Example 3 were used. Samples were prepared by diluting the 100 ng/5 µL MKN45 RNA (equivalent to $10^4$ cells) with the 120 ng/5 µL white blood cell RNA (equivalent to $10^4$ cells) in 10-fold steps to MKN45 RNA concentrations equivalent to $10^3$ cells, $10^2$ cells and $10^1$ cells. As the negative sample, the 120 ng/5 µL white blood cell RNA (equivalent to $10^4$ cells) was used. CEA RNA was assayed at $10^3$ copies/5 µl and $10^7$ copies/5 µl.

The assay data shown in FIG. 4 indicate that at least $10^1$ MKN45 cells can be detected in $10^4$ normal white blood cells. Nothing was detected in the normal white blood cell RNA (nega). The results demonstrate that the present invention enables detection of micrometastatic cancer cells in normal tissues.

EXAMPLE 5

CEA RNA at various initial copy numbers was detected using the combinations of oligonucleotide primers of the present invention, under the same conditions as in Example 3.

However, the first oligonucleotide primer had SEQ ID NO:20, the second oligonucleotide primer had SEQ ID NO:22 and the scissor oligonucleotide primer had SEQ ID NO:21. The second oligonucleotide primer additionally had SEQ ID NO:23 (the promoter sequence for T7 polymerase) at the 5' end.

FIG. 5 shows the time courses of the ratio of fluorescence intensities of the samples (fluorescence intensity at a certain time/background fluorescence intensity) from addition of the enzyme solution at 0 minute at the initial amounts of the CEA RNA of from $10^7$ copies/30 µl to $10^2$ copies/30 µl. The fluorescence profiles were dependent on the initial CEA RNA concentrations as shown in FIG. 5 and suggest that it is possible to quantify the CEA RNA in an unknown sample.

Further, as compared with the results of Example 3, the detection time for the respective initial copy numbers is short. This suggests that it is possible to provide particularly fast detection by the combinations of primers of this Example.

As described above, the present invention makes it possible to amplify and detect a specific RNA sequence in tumor cells at relatively low and constant temperatures (from 35° C. to 50° C., preferably 44° C.) in one step in a short time and therefore is applicable to detection of intraoperative detection of micrometastasis of tumor cells.

In the present invention, it is possible to determine an initial amount of a target RNA (a specific sequence in a tumor cell RNA) in a sample in a short time easily by synthesizing a double-stranded DNA having a promoter region for a DNA-dependent DNA polymerase from the target RNA, then synthesizing a large amount of RNA single strands from the double-stranded DNA to increase the single-stranded RNA production exponentially, measuring the fluorescence enhancement resulting from hybridization of a fluorescent intercalative dye-labeled probe with the RNA transcript and analyzing the enhancement of the fluorescence intensity.

Because the present invention can be carried out isothermally, ready-made detection kits for plural different target RNAs (specific RNA sequences in tumor cells) can be used with the same instrument simultaneously and therefore enable detection of metastases of different kinds of tumors.

The present invention also provides combinations of oligonucleotides used for detection of a specific sequence in a tumor cell RNA, i.e., combinations of oligonucleotide primers for amplification of a specific sequence in a tumor cell RNA and oligonucleotides for detection of the specific sequence in a tumor cell RNA and thereby provides a simple, fast and sensitive method of detecting tumor cell micrometastases and a detection kit using them.

The entire disclosure of Japanese Patent Application No. 2003-129360 filed on May 7, 2003 including specification, claims, drawings and summary is incorporated herein by reference in its entirety.

The invention claimed is:

1. A method of detecting micrometastasis of cells of a tumor in a sample obtained from a region of a subject other than a primary focus of the tumor, the method comprising
(1) synthesizing a cDNA with a primer consisting of SEQ ID NO:20, optionally with a promoter sequence for an RNA polymerase at the 5' end and an enzyme having RNA-dependent DNA polymerase activity from the sample,
(2) degrading the RNA in the cDNA with an enzyme having ribonuclease H activity to produce a single-stranded DNA,
(3) forming a double-stranded DNA with an oligonucleotide consisting of SEQ ID NO:22, optionally with a promoter sequence for an RNA polymerase at the 5' end and an enzyme having DNA-dependent DNA polymerase activity,
(4) transcribing the double-stranded DNA into an RNA transcript with an enzyme having RNA polymerase activity; and
(5) detecting the mRNA, wherein the presence of mRNA in the sample is indicative of micrometastasis of cells of a tumor in the subject,
   wherein the primer consisting of SEQ ID NO:20 or SEQ ID NO:22 has a promoter sequence for an RNA polymerase at the 5' end.

2. The method according to claim 1, wherein the RNA from tumor cells is carcinoembryonic antigen (CEA) RNA.

3. The method of claim 1, which is isothermic.

4. The method of claim 1, which is performed at a temperature of from 35 to 50° C.

5. The method of claim 1, which is performed at a temperature of about 44° C.

6. A method of detecting micrometastasis of cells of a tumor in a sample obtained from a region of a subject other than a primary focus of the tumor, the method comprising,
   mixing the sample with a reaction solution and an enzyme solution,
   incubating the mixture at a temperature of from 35 to 50° C. for a time to generate RNA, and
   detecting the RNA generated, wherein the presence of mRNA in the sample is indicative of micrometastasis of cells of a tumor in the subject,
   wherein the reaction solution is a buffered solution comprising deoxyribonucleotides, ribonucleotides, an oligonucleotide consisting of SEQ ID NO:20, optionally with a promoter sequence for an RNA polymerase at the 5' end, an oligonucleotide consisting of SEQ ID NO:21, and an oligonucleotide consisting of SEQ ID NO:22, optionally with a promoter sequence for an RNA polymerase at the 5' end, and
   wherein the enzyme solution comprises an RNA-dependent DNA polymerase and an RNA polymerase
   wherein the primer consisting of SEQ ID NO:20 or SEQ ID NO:22 has a promoter sequence for an RNA polymerase at the 5' end.

7. The method of claim 1, further comprising before (1), cleaving target RNA in the presence of an oligonucleotide comprioing consisting of SEQ ID NO:21.

* * * * *

SEQUENCE LISTING

<160> NUMBER OF SEQ ID NOS: 23

<210> SEQ ID NO 1
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 1
tttgtagctt gctgtgtcat                                              20

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
tattattcac agtgatgttg                                              20

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
agactgtgat cgtcgtgact                                              20

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
ttaattcgtt ctggattcca                                              20

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
ctggctgagt tattggcctg                                              20

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
gagtctgggg gggaaatgat                                              20

<210> SEQ ID NO 7
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 7
accccaatgc atccctgctg atc                                          23
```

```
<210> SEQ ID NO 8
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 8
tacaaatgtg aaacccagaa ccc                                              23

<210> SEQ ID NO 9
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 9
ataatagtgg atcctatacg tgc                                              23

<210> SEQ ID NO 10
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 10
cagtctatgc agagccaccc aaa                                              23

<210> SEQ ID NO 11
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 11
aattaagtgt tgaccacagc gac                                              23

<210> SEQ ID NO 12
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 12
agccagtggc cacagcagga cta                                              23

<210> SEQ ID NO 13
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 13
tggggtatat tatctctcga ccac                                             24

<210> SEQ ID NO 14
<211> LENGTH: 24
<212> TYPE: DNA
<213> ORGANISM: Artificial Sequence
<220> FEATURE:
<223> OTHER INFORMATION: synthetic oligonucleotide
```

<400> SEQUENCE: 14
tttgtagctt gctgtgtcat ttct                                      24

<210> SEQ ID NO 15
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 15
tattattcac agtgatgttg ggga                                      24

<210> SEQ ID NO 16
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 16
agactgtgat cgtcgtgact gtgg                                      24

<210> SEQ ID NO 17
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 17
ttaattcgtt ctggattcca cact                                      24

<210> SEQ ID NO 18
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 18
ctggctgagt tattggcctg gcag                                      24

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
tgctggagat ggagggcttg                                           20

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20
gttcacaggt gaaggccaca                                           20

<210> SEQ ID NO 21

```
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 21
tgttggagat aaagagctct tgtg                                              24

<210> SEQ ID NO 22
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 22
ccaacatcac tgagaagaac agc                                               23

<210> SEQ ID NO 23
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 23
aattctaata cgactcacta tagggaga                                          28
```